(12) United States Patent
Chen

(10) Patent No.: US 6,353,757 B2
(45) Date of Patent: Mar. 5, 2002

(54) METHOD FOR COLLECTING DATA PERTINENT TO PREDICTORS OF HEART ARRHYTHMIAS USING AN ANIMAL TEST SUBJECT

(75) Inventor: Peng-Sheng Chen, La Canada, CA (US)

(73) Assignee: Cedars-Sinai Medical Center, Los Angeles, CA (US)

(*) Notice: Subject to any disclaimer, the term of this patent is extended or adjusted under 35 U.S.C. 154(b) by 0 days.

(21) Appl. No.: 09/884,212

(22) Filed: Jun. 18, 2001

Related U.S. Application Data

(62) Division of application No. 09/307,230, filed on May 7, 1999.

(51) Int. Cl.⁷ .................................................. A61N 1/00
(52) U.S. Cl. ............................ 607/3; 128/898; 600/508
(58) Field of Search ..................... 607/1–3, 72; 128/877, 128/898; 600/508, 515, 518

(56) References Cited

U.S. PATENT DOCUMENTS

| 5,147,294 A |   | 9/1992 | Smith et al. |
| 5,203,326 A | * | 4/1993 | Collins ........................... 607/9 |
| 5,921,940 A |   | 7/1999 | Verrier et al. |

FOREIGN PATENT DOCUMENTS

| EP | 0047013 A1 | 3/1982 |
| EP | 0547734 A3 | 6/1993 |
| EP | 0547734 A2 | 6/1993 |
| WO | WO 99/07354 A2 | 2/1999 |

OTHER PUBLICATIONS

PCT International Search Report re PCT/US00/12367, mailed Aug. 11, 2000.

(List continued on next page.)

Primary Examiner—George R. Evanisko
(74) Attorney, Agent, or Firm—Sidley Austin Brown & Wood

(57) ABSTRACT

A method is described for increasing the likelihood of the occurrence of an arrhythmia in a heart, particularly a ventricular arrhythmia of the type leading to Sudden Cardiac Death. The method includes the steps of creating an atrioventricular block in the heart of an animal test subject, inducing a myocardial infarction in the heart of the test subject, and then stimulating myocardial hyperinnervation the test subject. In a specific example described herein, the atrioventricular block is created by ablating the atrioventricular node of the heart using an ablation catheter. The myocardial infarction is induced by ligating the left anterior descending portion of the coronary artery. Myocardial hyperinnervation is stimulated by application of Nerve Growth Factor or other neurotrophic vectors to the left stellate ganglion. The test subject is an adult canine. By creating an atrioventricular block and a myocardial infarction within the heart of an adult canine test subject, then stimulating nerve growth within the left stellate ganglion of the subject using Nerve Growth Factor, it has been found that there is a significant increase in the likelihood of Sudden Cardiac Death arising from ventricular arrhythmias. It is believed that the Sudden Cardiac Death of the test subject arises in a manner very similar to circumstances wherein Sudden Cardiac Death occurs in human patients subject to a previous myocardial infarction, thus, an animal model system for artificially inducing a heart arrhythmia is also disclosed. Thus, the method and animal model system facilitate the collection of data pertinent to conditions within the heart arising prior to Sudden Cardiac Death and for developing and testing therapies intended to prevent Sudden Cardiac Death.

4 Claims, 2 Drawing Sheets

OTHER PUBLICATIONS

Malkin, Robert A. et al., The Effect of Inducing Ventricular Fibrillation with 50–hz Pacing Versus T Wave Stimulation on the Ability to Defibrillate, *PACE*, 21:1093–1097 (May 1998).

Schwartz, P.J., et al. "Autonomic Mechanisms in Ventricular Fibrillation Induced by Myocardial Ischemia During Exercise in Dogs with Healed Myocardial Infarction. An Experimental Preparation for Sudden Cardiac Death." PubMed Abstract of *Circulation* Apr.; 69(4): 790–800 )1984.

* cited by examiner

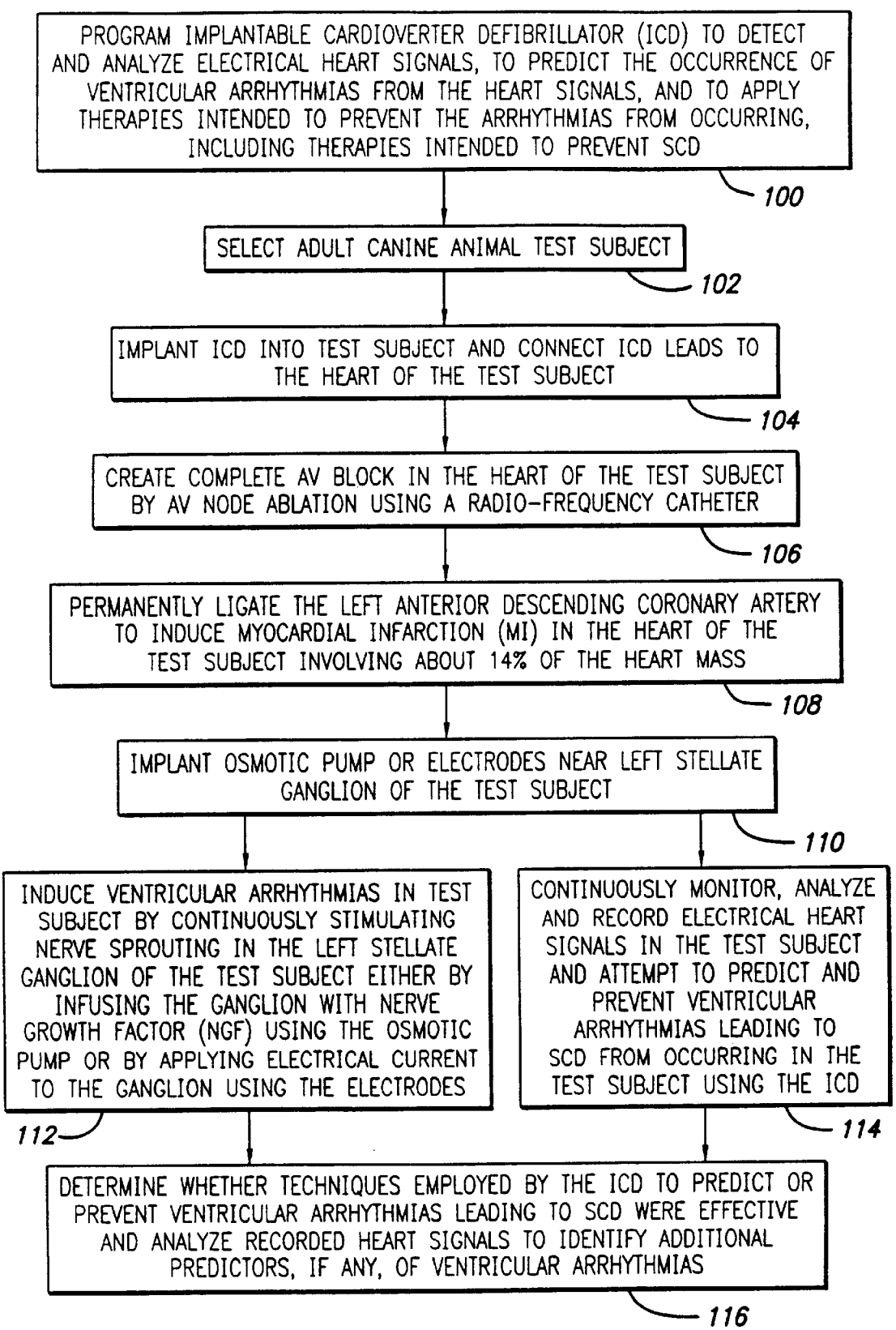

METHOD FOR COLLECTING DATA PERTINENT TO PREDICTORS OF HEART ARRHYTHMIAS USING AN ANIMAL TEST SUBJECT

This application is a division of U.S. Ser. No. 09/307,230, filed on May 7, 1999. This application is also related to U. S. Ser. No. 09/884,520, filed Jun. 18, 2001, which is also a divisional application of U.S. Ser. No. 09/307,230, filed May 7, 1999.

FIELD OF THE INVENTION

The invention generally relates to techniques for inducing heart arrhythmias in animal test subjects and in particular to techniques for inducing ventricular arrhythmias of the type that can result in Sudden Cardiac Death.

BACKGROUND OF THE INVENTION

Sudden Cardiac Death ("SCD") claims about 300,000 lives a year in the United States alone. In most cases, the direct cause of SCD is a ventricular tachycardia ("VT") which triggers a ventricular fibrillation ("VF"). VT and VF are different types of ventricular arrhythmias. VT is an abnormally fast ventricular heart rhythm which is, by itself, typically not fatal. VF is a chaotic ventricular heart rhythm which produces little or no net blood flow from the heart, such that there is little or no net blood flow to the brain and other organs. VF, if not terminated, results in death. In most cases of SCD, the victim has a previous myocardial infarction ("MI"), i.e. the patient had a previous heart attack caused by blockage of a portion of the coronary artery which supplies blood to the heart muscle. As a result of the blockage, a portion of the heart muscle does not receive blood and therefore becomes scarred and diseased. The scarred and diseased portion of the heart is referred to as the MI. For several days immediately subsequent to the occurrence of an MI, numerous episodes of VT—referred to as phase one episodes—typically occur. Eventually, the phase one VT episodes largely disappear. Several days or weeks later, though, additional episodes of VT—referred to as phase two episodes—typically begin to occur. It is the phase two episodes of VT that often transition to VF resulting in SCD of the patient.

Accordingly, it would be highly desirable to develop techniques for preventing VT from occurring, particularly phase two VT in a patients having an MI and, if VT does occur, for preventing the VT from transitioning to a VF. One technique employed in an attempt to prevent VT from occurring is overdrive pacing of the heart. With overdrive pacing, the heart is paced at a rate higher than its intrinsic pacing rate. If VT nevertheless occurs, one or more electrical cardioversion pulses are typically applied to the heart in an attempt to terminate the VT so that the VT does not transition to VF. If VF nevertheless occurs, one or more stronger electrical defibrillation pulses are typically applied to the heart in an attempt to terminate the VF thereby preventing SCD. Hence, for patients that have an MI, particularly a significant one, an implantable cardioverter-defibrillator (ICD) is often implanted into the patient. The ICD includes components for overdrive pacing the heart and for detecting VT or VF and for administering the appropriate therapy. However, the need to frequently overdrive pace the heart and to deliver cardioversion or defibrillation pulses can quickly deplete the battery power of the ICD requiring frequent replacement. Also, the therapies administered by the ICD, particularly the application of cardioversion pulses, may be extremely painful to the patient. Moreover, in some cases, the conventional therapy provided by the ICD is not sufficient to prevent or terminate VF and, accordingly, the patient succumbs to SCD.

Hence, it would also be highly desirable to develop new and more effective techniques for predicting and preventing VT from occurring, particularly prevention techniques that do not require frequent overdrive pacing. For example, it would be desirable to provide a technique for predicting when an episode of VT is imminent such that overdrive pacing, or other therapies, need only be applied in circumstances when VT is likely to occur. A reliable prediction technique could greatly reduce need for overdrive pacing, thereby substantially extending the lifetime of the power supply of the ICD and eliminating the need for frequent surgical replacement of the battery supply. Most importantly, with reliable VT prediction, techniques for preventing the occurrence of VT may prove to be more reliable, thus reducing the number of episodes of VT and consequently reducing the need for cardioversion therapy and reducing the risk that the VT may transition to VF if cardioversion fails.

It would also be highly desirable to develop new and more effective techniques for predicting and preventing VT from transitioning to VF, preferably without the need for cardioversion pulses. For example, it would be desirable to provide a technique for predicting when an episode of VT is likely to transition to VF such that cardioversion therapy need only be applied when there is a significant risk that the transition will occur. A reliable prediction technique could greatly reduce the need for cardioversion therapy which, as noted, can be extremely painful to the patient. Also the lifetime of the power supply of the ICD is further extended thus reducing the need for surgical replacement procedures. Most importantly, with reliable VF prediction, techniques for preventing the occurrence of VF may prove to be more reliable, thus reducing the number of episodes of VF and consequently reducing the need for defibrillation therapy and reducing the risk of SCD if defibrillation fails.

The new and more effective prediction or prevention techniques could take the form of new detection or analysis techniques performed by the ICD, or new therapies administered by the ICD. Alternatively, the techniques could take the form of therapies not requiring implantation of an ICD, such as application of new drug therapies and the like. Considerable research is ongoing in these areas.

A significant problem, however, is that there is currently no effective technique for inducing ventricular arrhythmias in test animals, particularly ventricular arrhythmias of the type resulting in SCD, in such a manner that permits effective testing of techniques intended to predict and prevent the arrhythmias to thereby prevent SCD. More specifically, it would be highly desirable to provide a technique for inducing VT or VF within test animals which would permit researchers to analyze conditions within the heart leading up to VT or VF for the purposes of identifying conditions which might serve to predict VT or VF. A technique for reliably inducing VT or VF within test animals, would also assist researchers in developing and testing new techniques for preventing VT or VF from occurring and for evaluating the efficacy of such techniques. As one example, therapies for the purposes of preventing VT from transitioning to VF without requiring a cardioversion pulse could be tested by implanting an ICD within an animal test subject, then inducing VT to thereby verify that the ICD reliably prevents the VT from transitioning to VF and thereby prevents or at least reduces the risk of SCD. Such tests would also prove helpful in gaining government approval for marketing ICD's or other implantable medical devices intended to prevent SCD.

More specifically, there appear to be no effective techniques for inducing VT or VF within test animals which effectively reproduce the conditions with which SCD typically occurs in human patients, i.e., phase two VT to VF transitions within patients subject to a previous MI. One conventional technique, for example, requires applying electrical stimulation pulses to the heart to artificially induce VT. However, if VT is artificially induced by application of electrical pulses, any characteristics of naturally occurring VT which could act as a reliable predictor of a subsequent transition to VF are difficult, and perhaps impossible, to detect. Likewise, techniques intended to prevent the VT to VF transition are difficult to test in circumstances where artificial electrical pulses are simultaneously being applied to the heart. Rather, reliable testing of techniques for predicting and preventing a VT to VF transition are best performed if the VT to VF transition arises in substantially the same manner in which it would naturally arise within patients, particularly those patients already subject to an MI.

Another conventional technique for artificially inducing SCD within test animals, is to create an acute ischemia sufficient to induce VT. An acute ischemia is a complete or nearly complete loss of blood supply to the heart typically resulting in a massive MI and death of the test subject. Techniques intended to predict or prevent a VT or a VF within patients having a mild MI may not be effectively tested in circumstances where a much more severe ischemia is imposed upon the heart of the test animal. Furthermore, many SCD episodes are not associated with any evidence of ischemia. Therefore, induction of SCD by ischemia does not necessarily simulate what actually happens in patients.

Thus, it would be highly desirable to provide a technique for inducing arrhythmias in animal test subjects, which induces the arrhythmias in a manner similar to which arrhythmias normally occur within human patients. In particular, it would be highly desirable to provide a technique for inducing ventricular arrhythmias of the type leading to SCD in patients having a previous MI. It is to these ends that the invention is primarily directed.

SUMMARY OF THE INVENTION

In accordance with one aspect of the invention, a method is provided for increasing the likelihood of the occurrence of an arrhythmia in a heart, particularly a ventricular arrhythmia of the type leading to SCD. The method includes the steps of creating an atrioventricular (AV) block in the heart of an animal test subject, inducing an MI in the heart of the test subject, and then stimulating myocardial hyperinnervation in the test subject.

In an exemplary embodiment of the method, the AV block is created by ablating the AV node of the heart using an ablation catheter. The MI is induced by ligating the left anterior descending portion of the coronary artery. Myocardial hyperinnervation is stimulated by application of nerve growth factor ("NGF") or other neurotrophic vectors to the left stellate ganglion. Alternatively, electrical stimulation signals are applied to the left stellate ganglion. The test subject may be, for example, an adult canine.

By creating an AV block and an MI within the heart of an adult canine test subject, then stimulating nerve growth within the left stellate ganglion of the subject using NGF, it has been found that there is a significant increase in the likelihood of SCD arising from phase two ventricular arrhythmias. It is believed that the SCD of the test subject arises in a manner very similar to circumstances wherein SCD occurs in human patients subject to a previous MI. Thus, the method permits SCD to be induced within test animals in a manner facilitating the collection of data pertinent to conditions within the heart arising prior to SCD and for testing techniques intended to prevent SCD, particularly techniques intended to prevent phase two VT and VF within patients subject to a previous MI. Hence, other aspects of the invention are directed to methods for collecting data pertinent to predictors of arrhythmias, particularly phase two VT and VF in patients subject to a previous MI, to facilitate development of techniques for predicting and preventing the arrhythmias. Still other aspects of the invention are directed to methods for testing techniques intended to predict or prevent the onset of arrhythmias, again particularly phase two VT and VF in patients subject to a previous MI. Still other objects, advantages and features of the invention will be apparent from the detailed descriptions which follow in combination with the attached drawings.

BRIEF DESCRIPTION OF THE DRAWINGS

FIG. 2 illustrates a method for inducing ventricular arrhythmias in the animal test subject of FIG. 1 and for testing the ICD to verify that the ICD properly predicts or prevents the arrhythmias.

DETAILED DESCRIPTION OF THE EXEMPLARY EMBODIMENTS

Figure 1:
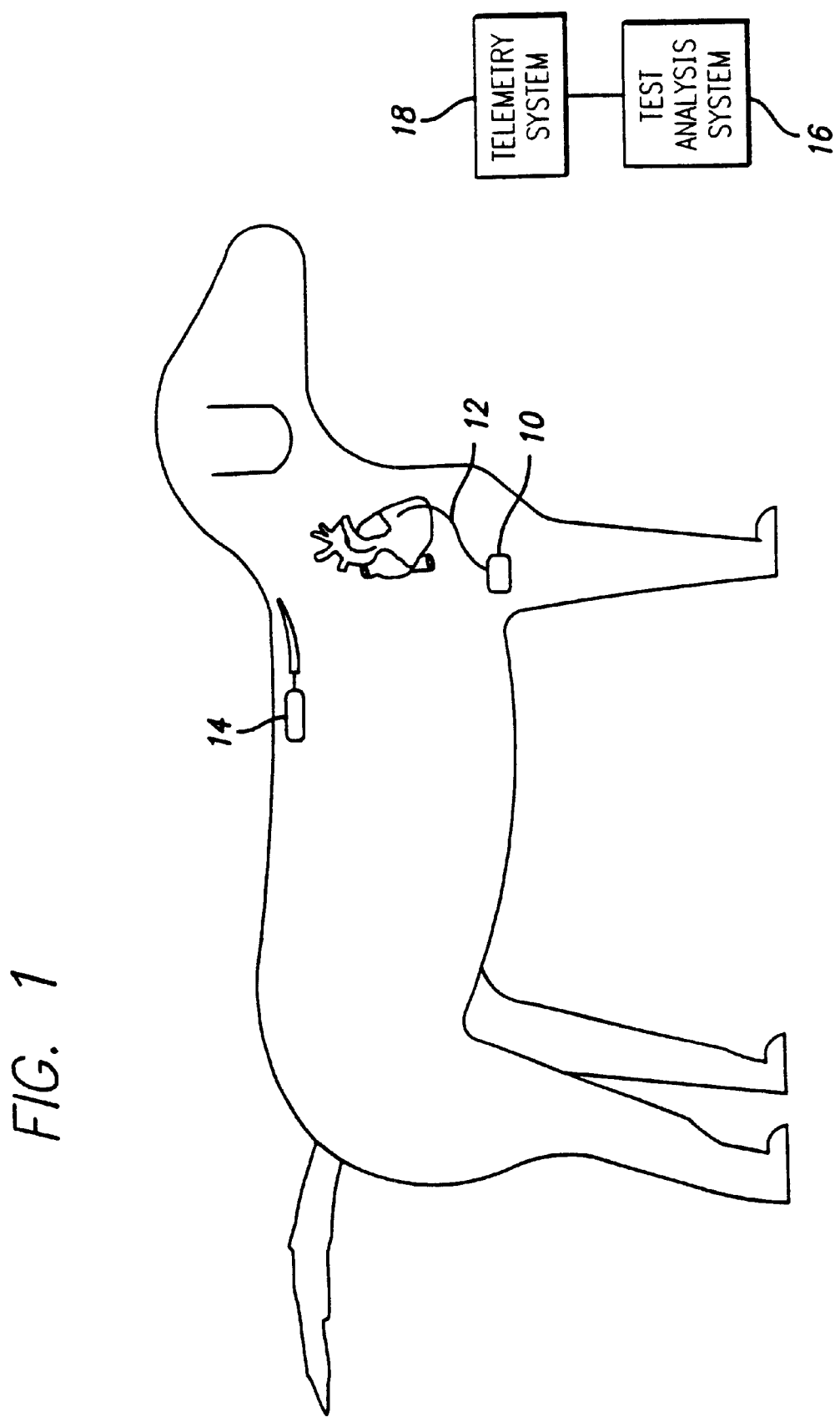
FIG. 1 is a stylized representation of an animal test subject having an osmotic pump and ICD implanted therein and particularly illustrating the heart and left stellate ganglion of the test subject.

Referring to the figures, various techniques for inducing ventricular arrhythmias of the type leading to SCD within animal test subjects will now be described. The techniques for inducing ventricular arrhythmias are described primarily with reference to the testing of therapies intended to prevent SCD, wherein the therapies are administered by an ICD. However, the techniques for inducing ventricular arrhythmias are also applicable to a wide range of other practical applications such as the testing of therapies that do not involve ICD's.

Briefly, in one example, the technique for inducing ventricular arrhythmias involves creating an AV block in the heart of an animal test subject, inducing an MI in the test subject and stimulating hyperinnervation in the left stellate ganglion of the test subject by pumping NGF or other neurotrophic vector into the ganglion using an osmotic pump. FIG. 1 is a stylized illustration of an animal test subject, particularly illustrating the heart and left stellate ganglion of the subject. FIG. 1 also illustrates an ICD 10 having a lead 12 coupled to the heart and an osmotic pump 14 positioned near the left stellate ganglion. Osmotic pump 14 continuously infuses the left stellate ganglion with NGF to stimulate nerve sprouting therein which, as will be described below, increases the likelihood of ventricular arrhythmias, particularly arrhythmias of the type possibly leading to SCD. ICD 10 is programmed to predict and prevent the ventricular arrhythmias in the heart of the test subject. To this end, the ICD detects and records electrical signals from the heart using lead 12 and, if necessary, applies therapy to the heart using the lead. The programs of the ICD are preferably newly developed prediction or prevention techniques in need to test verification. A test analysis system 16, which may include a conventional ICD programmer device or other computing device, interrogates the ICD using a telemetry system 18 to download the recorded heart signals for analysis for determining whether the ICD properly predicts and prevents ventricular arrhythmias.

The techniques for inducing ventricular arrhythmias in animal test subjects and for testing techniques intended to predict or prevent the arrhythmias will now be described in detail with reference to FIG. 2. Initially, at step 100, an ICD is programmed to detect and analyze electrical heart signals and to attempt to predict therefrom the occurrence of arrhythmias, particularly ventricular arrhythmias that may lead to SCD. The ICD is also programmed to apply therapy in an attempt to prevent the ventricular arrhythmias from occurring and thereby prevent SCD. The specific ICD programming for predicting or preventing ventricular arrhythmias may be consistent with conventional techniques. Preferably, though, the ICD is programmed to implement newly developed techniques for prediction or prevention of arrhythmias.

As far as conventional prediction techniques are concerned, the ICD may be programmed to predict whether VF is imminent by detecting the occurrence of VT and then determining the rate of the VT. If the rate is above a certain threshold, the ICD concludes that a transition to VF is likely. Prevention of VF may then be attempted using conventional cardioversion therapy. As far as conventional prevention techniques are concerned, the ICD may be programmed to overdrive pace the heart in an attempt to prevent the occurrence of phase two VT. A wide range of other conventional prediction or prevention techniques may be employed.

Newly developed techniques for prediction or prevention of ventricular arrhythmias may exploit unique characteristics of heart signals occurring prior to the onset of VT or perhaps occurring during VT but prior to a transition to VF. As can be appreciated, a wide variety of techniques for predicting or preventing ventricular arrhythmias may be programmed for use with the ICD. The ICD may be programmed to perform multiple concurrent techniques. The ICD may additionally perform other functions, such as anti-bradycardia pacing, not specifically targeted for the prediction or prevention of ventricular arrhythmias leading to SCD.

At step 102, an animal test subject such as an adult mongrel canine is selected and, at step 104, the ICD is implanted within the test subject and appropriate leads are connected to the heart of the subject. At step 106, a complete AV block is created within the heart of the animal test subject by ablation of the AV node using a radio frequency catheter, or other appropriate device or technique. If the animal test subject is an adult canine, the heart typically continues to beat without the need for any pacing. For other animal test subjects, pacing may be required. Accordingly, in such subjects, the ICD should be programmed to provide the appropriate pacing. For adult canines, the AV node is preferably completely ablated to provide a total AV block. For other animal test subjects, a partial AV block may suffice and, indeed, for some animal test subjects it is possible that other aspects of the invention described herein are sufficient to reliably induce ventricular arrhythmias without any AV blockage. The identification of such test subjects, if any, is achieved using routine techniques such as by experimenting with different test subjects, some having a complete AV block and others having only partial or non-existent AV blocks.

At step 108, the left anterior descending coronary artery of the animal test subject is completely ligated below the first diagonal branch to create an MI. Alternative techniques for blocking the coronary artery to create an MI include injecting certain block-inducing chemicals into the artery or positioning wires or other blocking devices into the artery using a catheter. For adult canines, it has been found that the aforementioned ligation typically results in an MI involving about 14% of the heart of the animal test subject and that a 14% MI is effective for the purposes of the invention. Other degrees of MI may be found to be effective in adult canines as well including, for example, MI's involving between 10 to 30 percent of the heart. For some animal test subjects, a larger or smaller MI may be desirable. Depending upon the particular animal test subject, it may be desirable to provide additional or alternative ligation points within the coronary artery. As can be appreciated though, an MI affecting too great a portion of the heart of the animal test subject may result in immediate termination of the test subject, thereby preventing testing of the programs implemented by the ICD. Routine testing of various animal test subjects and of various locations for coronary artery ligation may be employed to determine an optimal amount of MI within selected animal test subjects so as to provide the highest likelihood of inducing ventricular arrhythmias of the type leading to SCD within the test subject.

At step 110, an osmotic pump is implanted within the animal test subject in the vicinity of the left stellate ganglion. Alternatively, electrodes are positioned in the vicinity of the left stellate ganglion. At step 112, the left stellate ganglion is continuously infused with NGF, or other neurotrophic vector, using the osmotic pump for the purposes of stimulating nerve sprouting or other forms of hyperinnervation within the left stellate ganglion or within the vicinity thereof. Other suitable neurotrophic vectors include neurotrophic chemicals, substances, hormones, etc. If electrodes are used, a low level electrical current is continuously conducted between the electrodes for the purposes of inducing nerve sprouting. Although continuous stimulation is preferred, intermittent or periodic stimulation may suffice for some test subjects. Also, although the stimulation of nerve sprouting in the left stellate nerve ganglion of adult canines has been found to be effective for the purposes of the invention, other myocardial nerve conduction areas may be effective as well in adult canines or in other animal test subjects. Routine experimentation may be performed to identify optimal locations for nerve hyperinnervation within the myocardial nerve pathways for different selected test animals. Also, depending upon the test subject, it may be desirable to provide both neurotrophic vector infusion and electrical stimulation either simultaneously or alternatingly. Other techniques or compounds for stimulating hyperinnervation may be found to be effective as well, in addition to neurotrophic vectors and electrical currents. Also, it may suffice for some test subjects to inject neurotrophic vectors into the left stellate ganglion rather than using an osmotic pump. For electrical stimulation, optimal current levels are determined by routine experimentation.

Thus, steps 106 and 112 serve to create a complete AV block and a mild MI in the animal test subject and to further induce myocardial hyperinnervation in the left stellate ganglion. It has been found that these steps result in a significant increase in the occurrence of ventricular arrhythmias of the type leading to SCD, specifically phase two VT and VF, within adult canine test subjects. It is believed that the ventricular arrhythmias induced as a result of steps 106–112 in a manner similar to those occurring within human patients subject to a prior MI and subject to complete or partial AV block. As such, the programs of the ICD can be tested in conditions closely resembling the conditions in which the ICD may need to operate if implanted in a human patient. Accordingly, simultaneous with step 112, step 114 is performed wherein the ICD monitors, analyzes and records conditions within the heart of the animal test subject and attempts to predict and prevent ventricular arrhythmias. Ultimately, at step 116, a determination is made as to whether the techniques performed by the ICD are effective, particularly techniques for preventing phase two VT and, if phase two VT nevertheless occurs, for preventing a transition to VF. If the techniques performed are not effective, such as if the ICD fails to prevent SCD within the animal test subject, the techniques are subsequently analyzed to determine the reasons for failure, perhaps resulting in adjustment of parameters used in connection with the programming of the ICD. If, on the other hand, SCD does not occur, this provides evidence as to the efficacy of the programs of the ICD. Of course, testing of the ICD is preferably performed against a suitably large population of animal test subjects to achieve statistically significant test results.

Whether or not SCD ultimately occurs, signals recorded during step 114 may be analyzed for the purpose of identifying any unique patterns within the heart signals which may serve as predictors for subsequent episodes of ventricular arrhythmias. For example, analysis of heart signals of a large number of animal test subjects wherein phase two VT occurs may reveal a correlation between certain features of the pre-VT heart signals and the subsequent occurrence of VT. If so, an ICD can be programmed to predict imminent VT in human patients based upon a detection of similar features of the heart signal and to apply preventative therapy, such as overdrive pacing, only if VT is predicted. Hence, unnecessary overdrive pacing is avoided. As another example, analysis of heart signals of a large number of animal test subjects wherein a VT to VF transition occurs may reveal a correlation between certain features of the pre-transition heart signals and the subsequent transition from VT to VF. If so, an ICD can be programmed to predict the imminent transition to VF in human patients based upon a detection of similar features of the pre-transition heart signal and to apply preventative therapy, such as aggressive cardioversion therapy, only if the transition to VF is expected. Hence, unnecessary cardioversion therapy is avoided. By using these and other predictive techniques, the lifetime of the power supply of the ICD can be extended and pain or discomfort associated with unnecessary therapy can be avoided.

Thus, the ventricular arrhythmias induced using steps 106–112 are helpful both for the purposes of testing techniques for predicting or preventing the arrhythmias and also for developing a database of heart signals prior to the occurrence of the arrhythmias for the purposes of developing new predictive and preventative techniques. Steps 106–112 need not be implemented only in connection with testing ICD therapies. Rather the techniques maybe implemented for use in testing a wide range of other predictive and preventative techniques, such as new drug therapies and the like.

As noted, for adult canine animal test subjects, hyperinnervation within the left stellate ganglion induced by NGF in combination with a complete AV block and a relatively mild MI has been found to significantly increase the likelihood of SCD within the animal test subjects. The increase in the likelihood of ventricular arrhythmias is believed to occur for the following reasons. It appears that an increase in sympathetic nerve activity may result in an increase in the likelihood of the ventricular arrhythmias. By inducing myocardial nerve sprouting, an increased myocardial sensitivity to sympathetic stimulation may occur thus increasing the likelihood of ventricular arrhythmias. Accordingly, to reduce the risk of SCD in human patients, it may be desirable to prevent nerve sprouting, particularly in the left stellate ganglion, for patients who have had an MI, and in particular for patients also having an AV block.

However, regardless of the particular mechanism from which the increased risk of SCD arises, the technique of the invention has been found effective in experiments conducted in connection with adult canines for statistically increasing the likelihood of SCD. The increase in likelihood of SCD was detected as compared to control subjects having only the MI and AV block, but not the myocardial hyperinnervation. An increase in the likelihood of phase two VT and VF episodes was also observed. In all subjects, a comparatively large number of phase one VT episodes was found to occur within five to ten days following creation of the MI within the test subjects. The occurrence of a large number of phase one VT episodes immediately following an MI is well known.

What has been described are various techniques for increasing the likelihood of ventricular arrhythmias in animal test subjects, particularly phase two VT arrhythmias of the type that often trigger VF and consequently SCD. Aspects of the techniques have been described primarily with reference to the flowchart of FIG. 2. Each block within the flowchart illustrates both a method step and an apparatus clement for performing the method step. Specific method steps may be performed, as described above, using an ICD, osmotic pump, ablation catheter, coronary artery ligature or other suitable devices. Many of the method steps need not necessarily be performed in the order illustrated. For example, the order in which the AV block and MI are created can be reversed. As another example, the order in which the osmotic pump and ICD are implanted can also be reversed.

In general, the method and apparatus embodiments illustrated with reference to the drawings and described herein are merely illustrative of principles of the invention which may be implemented in alternative embodiments to achieve other ends than those specifically described herein.

What is claimed:

1. A method for collecting data pertinent to predictors of heart arrhythmias, said method comprising the steps of:

creating an atrioventricular block in the heart of an animal test subject;

inducing a myocardial infarction in the heart of the animal test subject;

selecting a portion of the myocardium of the animal test subject wherein hyperinnervation is effective for increasing the likelihood of an arrhythmia;

stimulating myocardial hyperinnervation in the selected portion of the myocardium of the animal test subject;

detecting electrical signals in the heart;

detecting an occurrence of the arrhythmia; and recording the electrical signals that had been detected in the heart during at least a period of time prior to the detection of the occurrence of the arrhythmia.

2. The method of claim 1, wherein the step of recording the electrical signals is performed to also record electrical signals detected during the arrhythmia.

3. The method of claim 1, wherein the step of detecting the occurrence of the arrhythmia is performed to detect ventricular tachycardia.

4. The method of claim 1, wherein the step of detecting the occurrence of the arrhythmia is performed to detect ventricular fibrillation.

* * * * *